(12) United States Patent
Reinke et al.

(10) Patent No.: US 9,802,055 B2
(45) Date of Patent: Oct. 31, 2017

(54) ULTRASOUND POWERED PULSE DELIVERY DEVICE

(71) Applicant: Medtronic, Inc., Minneapolis, MN (US)

(72) Inventors: James D Reinke, Maple Grove, MN (US); Sarah A Audet, Shoreview, MN (US); Andrew J Ries, Lino Lakes, MN (US); Robert W Stadler, Shoreview, MN (US); John D Wahlstrand, Shoreview, MN (US); Zhongping Yang, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/140,637

(22) Filed: Apr. 28, 2016

(65) Prior Publication Data
US 2017/0281954 A1    Oct. 5, 2017

Related U.S. Application Data

(60) Provisional application No. 62/317,680, filed on Apr. 4, 2016.

(51) Int. Cl.
| A61N 1/00 | (2006.01) |
| A61N 1/378 | (2006.01) |
| A61N 1/365 | (2006.01) |
| A61N 1/37 | (2006.01) |

(52) U.S. Cl.
CPC ......... *A61N 1/3787* (2013.01); *A61N 1/365* (2013.01); *A61N 1/37* (2013.01)

(58) Field of Classification Search
CPC ......... A61N 1/3787; A61N 1/365; A61N 1/37
See application file for complete search history.

(56) References Cited

U.S. PATENT DOCUMENTS

| 4,280,502 A | 7/1981 | Baker, Jr. et al. |
| 4,374,382 A | 2/1983 | Markowitz |
| 4,485,813 A | 12/1984 | Anderson et al. |
| 4,787,389 A | 11/1988 | Tarjan |
| 4,830,006 A | 5/1989 | Haluska et al. |
| 4,865,037 A | 9/1989 | Chin et al. |
| 5,052,388 A | 10/1991 | Sivula et al. |

(Continued)

FOREIGN PATENT DOCUMENTS

| EP | 1541191 | 6/2005 |
| EP | 1961366 A1 | 8/2008 |

(Continued)

OTHER PUBLICATIONS

US 8,886,318, 11/2014, Jacobson et al. (withdrawn)

(Continued)

*Primary Examiner* — George Manuel

(57) ABSTRACT

An implantable device system for delivering electrical stimulation pulses to a patient's body includes a pulse delivery device having a piezoelectric element that is enclosed by a housing and produces voltage signals delivered to the patient's body in response to receiving ultrasound energy. The pulse delivery device includes a circuit having a rate limiter configured to filter voltage signals produced by the piezoelectric element a rate faster than a maximum stimulation rate.

23 Claims, 8 Drawing Sheets

(56) References Cited

U.S. PATENT DOCUMENTS

| | | |
|---|---|---|
| 5,113,859 A | 5/1992 | Funke |
| 5,117,824 A | 6/1992 | Keimel et al. |
| 5,144,950 A | 9/1992 | Stoop et al. |
| 5,174,289 A | 12/1992 | Cohen |
| 5,193,539 A | 3/1993 | Schulman et al. |
| 5,243,976 A | 9/1993 | Ferek-Petric et al. |
| 5,255,692 A | 10/1993 | Neubauer et al. |
| 5,331,966 A | 7/1994 | Bennett et al. |
| 5,354,316 A | 10/1994 | Keimel |
| 5,402,070 A | 3/1995 | Shelton et al. |
| 5,411,535 A | 5/1995 | Fujii et al. |
| 5,545,185 A | 8/1996 | Olson et al. |
| 5,593,431 A | 1/1997 | Sheldon |
| 5,620,474 A | 4/1997 | Koopman |
| 5,620,475 A | 4/1997 | Magnusson |
| 5,683,426 A | 11/1997 | Greenhut et al. |
| 5,749,909 A | 5/1998 | Schroeppel et al. |
| 5,814,089 A | 9/1998 | Stokes et al. |
| 5,817,130 A | 10/1998 | Cox et al. |
| 5,855,593 A | 1/1999 | Olson et al. |
| 5,861,018 A | 1/1999 | Feierbach |
| 5,893,882 A | 4/1999 | Peterson et al. |
| 5,897,583 A | 4/1999 | Meyer et al. |
| 5,928,271 A | 7/1999 | Hess et al. |
| 6,016,448 A | 1/2000 | Busacker et al. |
| 6,044,297 A | 3/2000 | Sheldon et al. |
| 6,108,579 A | 8/2000 | Snell et al. |
| 6,239,724 B1 | 5/2001 | Doron et al. |
| 6,256,534 B1 | 7/2001 | Dahl |
| 6,393,316 B1 | 5/2002 | Gillberg et al. |
| 6,411,842 B1 | 6/2002 | Cigaina et al. |
| 6,442,426 B1 | 8/2002 | Kroll |
| 6,477,420 B1 | 11/2002 | Struble et al. |
| 6,508,771 B1 | 1/2003 | Padmanabhan et al. |
| 6,522,915 B1 | 2/2003 | Ceballos et al. |
| 6,526,311 B2 | 2/2003 | Begemann |
| 6,592,518 B2 | 7/2003 | Denker et al. |
| 6,622,046 B2 | 9/2003 | Fraley et al. |
| 6,631,290 B1 | 10/2003 | Guck et al. |
| 6,738,668 B1 | 5/2004 | Mouchawar et al. |
| 6,754,528 B2 | 6/2004 | Bardy et al. |
| 6,788,971 B1 | 9/2004 | Sloman et al. |
| 6,904,315 B2 | 6/2005 | Panken et al. |
| 6,934,585 B1 | 8/2005 | Schloss et al. |
| 7,006,864 B2 | 2/2006 | Echt et al. |
| 7,031,772 B2 | 4/2006 | Condie et al. |
| 7,037,266 B2 | 5/2006 | Ferek-Petric et al. |
| 7,050,849 B2 | 5/2006 | Echt et al. |
| 7,181,284 B2 | 2/2007 | Burnes et al. |
| 7,184,830 B2 | 2/2007 | Echt et al. |
| 7,272,448 B1 | 9/2007 | Morgan et al. |
| 7,532,929 B2 | 5/2009 | Mussig et al. |
| 7,532,933 B2 | 5/2009 | Hastings et al. |
| 7,558,631 B2 | 7/2009 | Cowan et al. |
| 7,606,621 B2 | 10/2009 | Brisken et al. |
| 7,610,092 B2 | 10/2009 | Cowan et al. |
| 7,630,767 B1 | 12/2009 | Poore et al. |
| 7,634,313 B1 | 12/2009 | Kroll et al. |
| 7,680,538 B2 | 3/2010 | Durand et al. |
| 7,702,392 B2 | 4/2010 | Echt et al. |
| 7,702,395 B2 | 4/2010 | Towe et al. |
| 7,706,879 B2 | 4/2010 | Burnes et al. |
| 7,742,812 B2 | 6/2010 | Ghanem et al. |
| 7,742,816 B2 | 6/2010 | Masoud et al. |
| 7,751,881 B2 | 7/2010 | Cowan et al. |
| 7,765,001 B2 | 7/2010 | Echt et al. |
| 7,809,438 B2 | 10/2010 | Echt et al. |
| 7,848,815 B2 | 12/2010 | Brisken et al. |
| 7,881,791 B2 | 2/2011 | Sambelashvili et al. |
| 7,890,173 B2 | 2/2011 | Brisken et al. |
| 7,894,904 B2 | 2/2011 | Cowan et al. |
| 7,894,907 B2 | 2/2011 | Cowan et al. |
| 7,894,910 B2 | 2/2011 | Cowan et al. |
| 7,899,541 B2 | 3/2011 | Cowan et al. |
| 7,899,542 B2 | 3/2011 | Cowan et al. |
| 7,904,153 B2 | 3/2011 | Greenhut et al. |
| 7,930,027 B2 | 4/2011 | Prakash et al. |
| 7,937,148 B2 | 5/2011 | Jacobson |
| 7,937,159 B2 | 5/2011 | Lima et al. |
| 7,941,218 B2 | 5/2011 | Sambelashvili et al. |
| 7,949,404 B2 | 5/2011 | Hill |
| 7,953,493 B2 | 5/2011 | Fowler et al. |
| 7,991,467 B2 | 8/2011 | Markowitz et al. |
| 7,996,087 B2 | 8/2011 | Cowan et al. |
| 8,002,718 B2 | 8/2011 | Buchholtz et al. |
| 8,032,219 B2 | 10/2011 | Neumann et al. |
| 8,078,283 B2 | 12/2011 | Cowan et al. |
| 8,145,308 B2 | 3/2012 | Sambelashvili et al. |
| 8,160,684 B2 | 4/2012 | Ghanem et al. |
| 8,204,590 B2 | 6/2012 | Sambelashvili et al. |
| 3,214,041 A1 | 7/2012 | Van Gelder et al. |
| 8,249,717 B2 | 8/2012 | Brockway et al. |
| 8,265,770 B2 | 9/2012 | Toy et al. |
| 8,315,701 B2 | 11/2012 | Cowan et al. |
| 8,332,036 B2 | 12/2012 | Hastings et al. |
| 8,340,773 B2 | 12/2012 | Towe et al. |
| 8,364,276 B2 | 1/2013 | Willis |
| 8,369,956 B2 | 2/2013 | Towe et al. |
| 8,386,048 B2 | 2/2013 | McClure et al. |
| 8,391,964 B2 | 3/2013 | Musley et al. |
| 8,428,716 B2 | 4/2013 | Mullen et al. |
| 8,433,409 B2 | 4/2013 | Johnson et al. |
| 8,457,742 B2 | 6/2013 | Jacobson |
| 8,478,408 B2 | 7/2013 | Hastings et al. |
| 8,494,637 B2 | 7/2013 | Cowan et al. |
| 8,494,639 B2 | 7/2013 | Cowan et al. |
| 8,494,642 B2 | 7/2013 | Cowan et al. |
| 8,494,643 B2 | 7/2013 | Cowan et al. |
| 8,494,644 B2 | 7/2013 | Cowan et al. |
| 8,498,715 B2 | 7/2013 | Cowan et al. |
| 8,521,268 B2 | 8/2013 | Zhang et al. |
| 8,532,785 B1 | 9/2013 | Crutchfield et al. |
| 8,541,131 B2 | 9/2013 | Lund et al. |
| 8,588,909 B1 | 11/2013 | Levine |
| 8,588,926 B2 | 11/2013 | Moore et al. |
| 8,617,082 B2 | 12/2013 | Zhang et al. |
| 8,626,303 B2 | 1/2014 | Towe et al. |
| 8,630,716 B2 | 1/2014 | Brockway et al. |
| 8,630,717 B2 | 1/2014 | Olson et al. |
| 8,634,908 B2 | 1/2014 | Cowan |
| 8,639,333 B2 | 1/2014 | Stadler et al. |
| 8,649,875 B2 * | 2/2014 | Sarvazyan ............ A61B 8/0841 607/60 |
| 8,718,773 B2 | 5/2014 | Willis et al. |
| 8,744,572 B1 | 6/2014 | Greenhut et al. |
| 8,768,459 B2 | 7/2014 | Ghosh et al. |
| 8,774,928 B2 | 7/2014 | Towe et al. |
| 8,886,307 B2 | 11/2014 | Sambelashvili et al. |
| 8,886,311 B2 | 11/2014 | Anderson et al. |
| 8,909,351 B2 | 12/2014 | Dinsmoor et al. |
| 8,923,963 B2 | 12/2014 | Bonner et al. |
| 8,996,109 B2 | 3/2015 | Karst et al. |
| 9,008,776 B2 | 4/2015 | Cowan et al. |
| 9,014,803 B2 | 4/2015 | Cowan |
| 9,072,911 B2 | 7/2015 | Hastings et al. |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,278,218 B2 | 3/2016 | Karst et al. |
| 2002/0091421 A1 | 7/2002 | Greenberg et al. |
| 2004/0204744 A1 | 10/2004 | Penner et al. |
| 2004/0215308 A1 | 10/2004 | Bardy et al. |
| 2005/0197680 A1 | 9/2005 | DelMain et al. |
| 2005/0277990 A1 | 12/2005 | Ostroff et al. |
| 2006/0009818 A1 | 1/2006 | Von Arx et al. |
| 2006/0031378 A1 | 2/2006 | Vallapureddy et al. |
| 2006/0085041 A1 | 4/2006 | Hastings et al. |
| 2006/0149329 A1 | 7/2006 | Penner |
| 2006/0161061 A1 | 7/2006 | Echt et al. |
| 2006/0161205 A1 | 7/2006 | Mitrani et al. |
| 2006/0206165 A1 | 9/2006 | Jaax et al. |
| 2006/0235478 A1 | 10/2006 | Van Gelder et al. |
| 2006/0241705 A1 | 10/2006 | Neumann et al. |
| 2007/0049975 A1 | 3/2007 | Cates et al. |

(56) References Cited

U.S. PATENT DOCUMENTS

| | | |
|---|---|---|
| 2007/0088394 A1 | 4/2007 | Jacobson |
| 2007/0088398 A1 | 4/2007 | Jacobson |
| 2007/0106143 A1 | 5/2007 | Flaherty |
| 2007/0293900 A1 | 12/2007 | Sheldon et al. |
| 2008/0046038 A1 | 2/2008 | Hill et al. |
| 2008/0154322 A1 | 6/2008 | Jackson et al. |
| 2008/0269816 A1 | 10/2008 | Prakash et al. |
| 2008/0269823 A1 | 10/2008 | Burnes et al. |
| 2009/0036940 A1 | 2/2009 | Wei et al. |
| 2009/0036941 A1 | 2/2009 | Corbucci |
| 2009/0105782 A1 | 4/2009 | Mickle et al. |
| 2009/0234411 A1 | 9/2009 | Sambelashvili et al. |
| 2009/0234412 A1 | 9/2009 | Sambelashvili |
| 2009/0234413 A1 | 9/2009 | Sambelashvili et al. |
| 2009/0234414 A1 | 9/2009 | Sambelashvili et al. |
| 2009/0234415 A1 | 9/2009 | Sambelashvili et al. |
| 2009/0248103 A1 | 10/2009 | Sambelashvili et al. |
| 2010/0016911 A1 | 1/2010 | Willis et al. |
| 2010/0016914 A1 | 1/2010 | Mullen et al. |
| 2010/0023078 A1 | 1/2010 | Dong et al. |
| 2010/0042108 A1 | 2/2010 | Hibino |
| 2010/0152798 A1 | 6/2010 | Sanghera et al. |
| 2010/0198291 A1 | 8/2010 | Sambelashvili et al. |
| 2010/0228308 A1 | 9/2010 | Cowan et al. |
| 2010/0286541 A1 | 11/2010 | Musley et al. |
| 2010/0286744 A1 | 11/2010 | Echt et al. |
| 2011/0071586 A1 | 3/2011 | Jacobson |
| 2011/0184492 A1 | 7/2011 | Martens et al. |
| 2011/0190841 A1 | 8/2011 | Sambelashvili et al. |
| 2011/0196444 A1 | 8/2011 | Prakash et al. |
| 2011/0224744 A1 | 9/2011 | Moffitt et al. |
| 2011/0237967 A1 | 9/2011 | Moore et al. |
| 2012/0008714 A1 | 1/2012 | Rizwan |
| 2012/0035685 A1 | 2/2012 | Saha et al. |
| 2012/0109235 A1 | 5/2012 | Sheldon et al. |
| 2012/0109236 A1 | 5/2012 | Jacobson et al. |
| 2012/0172892 A1 | 7/2012 | Grubac et al. |
| 2012/0263218 A1 | 10/2012 | Dal Molin et al. |
| 2012/0296228 A1 | 11/2012 | Zhang et al. |
| 2012/0316613 A1 | 12/2012 | Keefe et al. |
| 2013/0013017 A1 | 1/2013 | Mullen et al. |
| 2013/0066169 A1 | 3/2013 | Rys et al. |
| 2013/0116738 A1 | 5/2013 | Samade et al. |
| 2013/0131750 A1 | 5/2013 | Stadler et al. |
| 2013/0131751 A1 | 5/2013 | Stadler et al. |
| 2013/0197599 A1 | 8/2013 | Sambelashvili et al. |
| 2013/0231710 A1 | 9/2013 | Jacobson |
| 2013/0268017 A1 | 10/2013 | Zhang et al. |
| 2013/0274828 A1 | 10/2013 | Willis |
| 2013/0282027 A1 | 10/2013 | Cowen et al. |
| 2013/0282070 A1 | 10/2013 | Cowan et al. |
| 2013/0282073 A1 | 10/2013 | Cowan et al. |
| 2014/0046420 A1 | 2/2014 | Moore et al. |
| 2014/0114372 A1 | 4/2014 | Ghosh et al. |
| 2014/0121720 A1 | 5/2014 | Bonner et al. |
| 2014/0207210 A1 | 7/2014 | Willis et al. |
| 2014/0330208 A1 | 11/2014 | Christie et al. |
| 2014/0330287 A1 | 11/2014 | Thompson-Nauman et al. |
| 2014/0330326 A1 | 11/2014 | Thompson-Nauman et al. |
| 2014/0358135 A1 | 12/2014 | Sambelashvili et al. |
| 2015/0100110 A1 | 4/2015 | Towe et al. |
| 2015/0112233 A1 | 4/2015 | Towe et al. |
| 2015/0142070 A1 | 5/2015 | Sambelashvili |
| 2015/0196755 A1 | 7/2015 | Cowan |
| 2015/0321011 A1 | 11/2015 | Carney et al. |
| 2015/0321016 A1 | 11/2015 | O'Brien et al. |
| 2016/0001086 A1 | 1/2016 | Towe et al. |
| 2016/0035967 A1 | 2/2016 | Moore et al. |

FOREIGN PATENT DOCUMENTS

| | | |
|---|---|---|
| EP | 2471452A1 A1 | 7/2012 |
| WO | 95/02995 | 2/1995 |
| WO | 2004002572 A1 | 1/2004 |
| WO | 2004/078252 A2 | 9/2004 |
| WO | 2006/133554 A1 | 12/2006 |
| WO | 2009006531 A1 | 1/2009 |

OTHER PUBLICATIONS

Greenhut, et al., Method and Apparatus for Selection and Use of Virtual Sensing Vectors, U.S. Appl. No. 14/524,090, filed Oct. 27, 2014, 57pp.

(PCT/US2015/029458) PCT Notification of Transmittal of the International Search Report and the Written Opinion of the International Searching Authority, mailed Aug. 25, 2015, 8 pages.

(PCT/US2015/029464) PCT Notification of Transmittal of the International Search Report and the Written Opinion of the International Searching Authority, Mailed Jul. 13, 2015, 9 pages.

(PCT/US2014/066792) PCT Notification of Transmittal of the International Search Report and the Written Opinion of the International Searching Authority.

(PCT/US2013/013601) PCT Notification of Transmittal of the International Search Report and the Written Opinion of the International Searching Authority.

Rodney Hawkins, "Epicardial Wireless Pacemaker for Improved Left Ventricular Reynchronization (Conceptual Design)", Dec. 2010, A Thesis presented to the Faculty of California Polytechnic State University, San Luis Obispo, 57 pp.

U.S. Appl. No. 14/801,049, filed Jul. 16, 2015.

(PCT/US2014/036782) PCT Notification of Transmittal of the International Search Report and the Written Opinion of the International Searching Authority, Mailed Aug. 22, 2014, 12 pages.

Ganapathy et al., "Implantable Device to Monitor Cardiac Activity with Sternal Wires," Pace, vol. 37, Dec. 2014, 11 pages.

Guenther et al., "Substernal Lead Implantation: A Novel Option to Manage DFT Failure in S-ICD patients," Clinical Research Cardiology, Published On-line Oct. 2, 2014, 3 pages.

Tung et al., "Initial Experience of Minimal Invasive Extra Cardiac Placement of High Voltage Defibrillator Leads," Canadian Cardiovascular Congress 2007, Oct. 2007, vol. 23, Supplement SC, Abstract 0697, http://www.pulsus.com/ccc2007/abs/0697.htm, 2 pages.

* cited by examiner

ULTRASOUND POWERED PULSE DELIVERY DEVICE

CROSS-REFERENCE TO RELATED APPLICATIONS

This application claims the benefit of U.S. Provisional Application No. 62/317,680, filed on Apr. 4, 2016. The disclosure of the above application is incorporated herein by reference in its entirety.

TECHNICAL FIELD

The disclosure relates generally to implantable medical devices and, in particular, to a system and method for delivering cardiac pacing without transvenous leads.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (A-V) node. The A-V node responds by propagating a ventricular depolarization signal through the bundle of His of the ventricular septum and thereafter to the bundle branches and the Purkinje muscle fibers of the right and left ventricles.

Conduction defects may occur along the intrinsic conduction pathways of the heart leading to irregularities in heart rate and asynchrony between heart chambers. Cardiac pacemakers are available to deliver electrical pacing pulses to one or more heart chambers to restore a more normal heart rhythm. Cardiac pacemakers may be coupled to one or more medical electrical leads to position electrodes at desired pacing sites, e.g., at endocardial pacing sites or within a cardiac vein. Single chamber leadless pacemakers have been proposed that carry electrodes on the housing of the pacemaker and may be implanted in a heart chamber without requiring a transvenous lead. The single chamber leadless pacemaker may sense cardiac electrical signals that indicate depolarization of the heart chamber in which the pacemaker is implanted and deliver pacing pulses in the same cardiac chamber when intrinsic cardiac events such as R-waves are not being sensed by the pacemaker to provide bradycardia pacing.

DETAILED DESCRIPTION

In the following description, references are made to illustrative embodiments for carrying out the methods described herein. It is understood that other embodiments may be utilized without departing from the scope of the disclosure.

Figure 1:
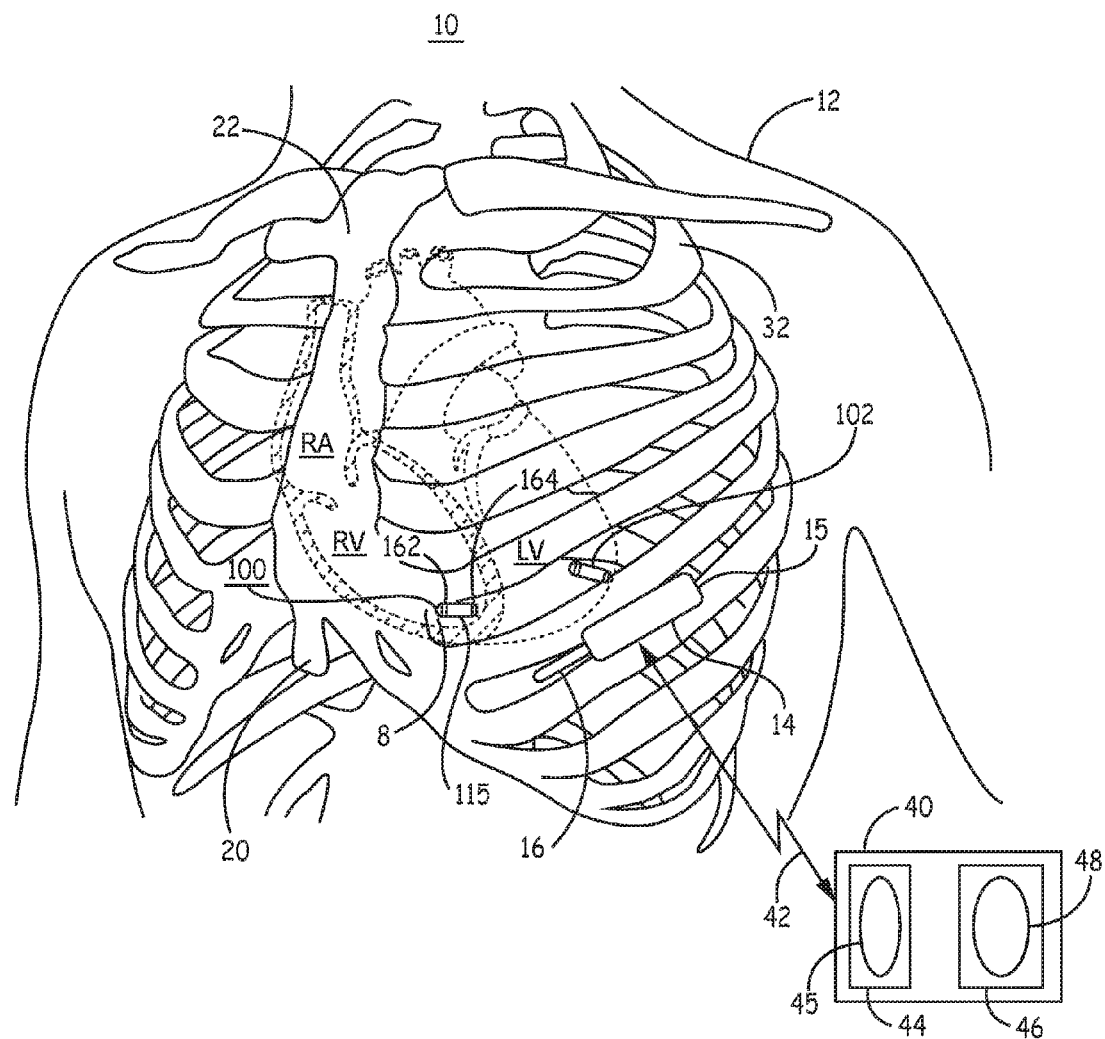
FIG. 1 is a conceptual diagram of an implantable medical device (IMD) system for delivering cardiac pacing according to one example.

FIG. 1 is a conceptual diagram of an implantable medical device (IMD) system 10 for delivering cardiac pacing according to one example. IMD system 10 includes a sensing and power transmission device 14, also referred to here as "sensing device 14," and a pulse delivery device 100. Sensing device 14 is implanted outside the cardiovascular system, e.g., subcutaneously, submuscularly, or substernally, and includes a housing 15 that encloses internal circuitry of sensing device 14, e.g., cardiac electrical sensing circuitry, a primary and/or rechargeable battery, electromechanical and/or thermal sensors to generate a signal correlated to patient activity, posture, temperature or other parameters used for controlling the timing and rate of pacing pulses, and power-transmitting circuitry as described below in conjunction with FIG. 3. Sensing device 14 may include one or more housing-based electrodes and/or an electrode extension 16 extending from housing 15 for carrying one or more electrodes for sensing cardiac electrical signals produced by the patient's heart 8, e.g., P-waves attendant to the depolarization of the atria of heart 8 and/or R-waves attendant to the depolarization of the ventricles of heart 8, and/or T waves attendant to the repolarization of the heart.

Pulse delivery device 100 is a miniaturized device configured to harvest power transmitted by sensing device 14 and deliver at least a portion of the transmitted power as pacing pulses to heart 8 to cause an evoked depolarization of the myocardium. Pulse delivery device 100 includes a housing 115 and a housing-based pacing electrode pair 162 and 164. Electrode 162 may be a ring electrode provided as an electrically conductive portion of housing 115 that serves as a return anode electrode during pacing pulse delivery. Electrode 164 may be a tip electrode provided as a cathode electrode electrically coupled to a circuit enclosed by housing 115 via an electrical feedthrough crossing housing 115. In other examples, electrodes 162 and 165 may both be provided as tip electrodes at opposing ends of pulse delivery device 100, both as ring electrodes at or near opposing ends of pulse delivery device 100, or as other types of electrodes extending from or incorporated along housing 115.

Pulse delivery device 100 is a passive device without an independent, active power source such as a battery that holds charge over a relatively long period of time, such as days, weeks, months or even years. Rather, pulse delivery device 100 may include dependent or passive elements, e.g. a piezoelectric material that produces a voltage signal when subjected to acoustical energy and one or more capacitors, resistors, transistors or other passive or dependent elements. A capacitor included in pulse delivery device provides temporary charge storage for delivering a pacing pulse. One or more capacitors may be charged for delivering one pacing pulse per charge/discharge cycle of the capacitor(s). For example, one or more storage or holding capacitors may be charged and discharged during a single cardiac pacing cycle as described in conjunction with FIGS. 5 and 6 below and may not be charged for storing and delivering energy required for delivering more than a single cardiac pacing pulse during a single charge/discharge cycle of the capacitor(s).

As described below in conjunction with FIG. 4, pulse delivery device 100 includes a power receiver enclosed by housing 115 provided as a piezoelectric element that produces a voltage signal in response to receiving ultrasound signals transmitted through the patient's body 12 at a resonant frequency of the piezoelectric material. The pulse delivery device 100 includes a circuit that is enclosed by housing 115 and receives voltage signals produced by the piezoelectric element. The circuit is configured to pass the voltage signals produced by the piezoelectric element in response to receiving ultrasound signals from sensing device 14 as electrical stimulation pulses and block voltage signals produced by the piezoelectric element in response to diagnostic ultrasound signals that may be applied to the patient's body for diagnostic purposes, for example during echocardiography or other imaging or Doppler ultrasound procedures. As disclosed herein, the pulse delivery device circuit blocks voltage signals produced by the piezoelectric element in response to ultrasound energy transmitted through the patient's body for diagnostic or imaging purposes by filtering and/or shunting voltage signals that are less than a minimum pacing pulse duration, greater than a maximum pacing pulse duration, and/or occur faster than a maximum pacing rate.

In some examples, sensing device 14 is configured to sense a cardiac electrical signal, identify cardiac events from the cardiac electrical signal and control a power transmitter to transmit a power signal to pulse delivery device 100. Sensing device 14 transmits the power signal to pulse delivery device 100 at an appropriate pacing interval following a cardiac event, e.g., following a P-wave or an R-wave, or following a preceding pacing pulse, to restore a more normal heart rhythm and/or cardiac chamber synchrony, e.g., when a conduction defect, atrial arrhythmia or other heart rhythm abnormality is present. Sensors incorporated in sensing device 14 may be used in determining the timing of the power transmission, monitor sensing device temperature, and/or monitor the patient's physiologic status. Sensing device 14 actively senses cardiac electrical signals and transmits power to the passive pulse delivery device 100, which has no cardiac signal sensing capabilities in some examples and passively generates a pacing pulse at the time of receiving the transmitted power.

In some examples, system 10 may include multiple pulse delivery devices, e.g., pulse delivery device 100 and pulse delivery device 102. In the example shown, pulse delivery device 102 is deployed along the left ventricle 9 of heart 8 for pacing the left ventricle. Pulse delivery device 102 may be deployed within a cardiac vein using a transvenous approach via the right atrium and coronary sinus. In other examples, pulse delivery device 102 may be implanted within the left ventricle (LV) along the endocardium or implanted epicardially, e.g., along the anterior, posterior, or lateral free wall or apex of the left ventricle. Pulse delivery device 100 is shown deployed along the right ventricle (RV) of the patient's heart 8 in the example of FIG. 1. Pulse delivery device 100 may be implanted endocardially using a transvenous approach via the right atrium (RA) at or near the right ventricular apex.

Pulse delivery devices 100 and 102 may include an active or passive fixation member, such as a single- or multi-tined fixation member, a hook, a helical screw, or other member that passively or actively engages with tissue at a target implant site, e.g., with the ventricular trabeculae, endocardium, epicardium, or cardiac vein inner walls. Pulse delivery device 100 is deployed and anchored at a first pacing site, e.g., along the right ventricle, and pulse delivery device 102 is deployed and anchored at a second pacing site spaced apart from the first pacing site, which may be in the same cardiac chamber such as within the right ventricle or both within the left ventricle, or a different cardiac chamber such as the left ventricle when pulse delivery device 100 is in the right ventricle. The locations of pulse delivery devices 100 and 102 in FIG. 1 are illustrative in nature and not intended to be limiting.

In the illustrative examples presented herein, pulse delivery device 100 is described as being deployed for delivering RV pacing pulses. However, pulse delivery devices 100 and 102 are not limited to ventricular pacing applications. In other examples, a pulse delivery device 100 may be deployed in, along or outside an atrial chamber or a ventricular chamber for delivering cardiac pacing pulses. In still other examples, pulse delivery device 100 is not limited to delivering cardiac pacing pulses and may be positioned along a nerve or other excitable tissue for delivering other types of electrical stimulation pulses to the patient's body 12, such as a neurostimulation therapy, which may be delivered along the spinal cord, vagal nerve, phrenic nerve, a skeletal muscle nerve, sensory nerve, brain, etc.

Sensing device 14 is deployed to an extra-cardiovascular location selected to enable acquisition of a cardiac electrical signal with acceptable signal-to-noise ratio for processing and analysis that allows reliable sensing and identification of cardiac events, e.g., at least R-waves, at least P-waves and R-waves, or at least P-waves, R-waves and T-waves. The implant location of sensing device 14 is also selected to enable acceptable power transmission efficiency to at least pulse delivery device 100 and pulse delivery device 102, if present. In other examples, multiple sensing devices may be implanted at extra-cardiovascular locations, each paired with a designated pulse delivery device 100 or 102. The separate implantation sites of each of the multiple sensing devices may be selected to provide optimal sensing of cardiac events used to set pacing timing intervals for controlling power transmission time to the respective pulse delivery device and to provide acceptable power transmission efficiency to the respective pulse delivery device.

For example, if sensing device 14 is implanted subcutaneously along a left intercostal space of ribcage 32 for transmitting power to pulse delivery device 100 positioned along the RV, a second sensing device may be implanted for transmitting power to pulse delivery device 102 implanted along the LV. The second sensing device may be implanted substernally, subcutaneously along a right intercostal space, or subcutaneously along a left intercostal space but medially, superiorly or inferiorly to sensing device 14. When more than one sensing device is included in system 10, the multiple sensing devices may be positioned along a common intercostal space but at different medial or lateral locations or along different intercostal spaces at the same or different medial or lateral locations.

Sensing extension 16 is provided to extend at least one electrode away from housing 15 to provide a sensing vector having greater inter-electrode spacing and having an angle relative to the heart axis that maximizes the signal strength of desired cardiac events, e.g., P-waves. Sensing extension 16 may be provided as a removable or non-removable member of sensing device 14 but may be coupled to sensing device 14 prior to implantation to provide one-step placement of sensing device 14 with sensing extension 16 already fixedly attached to housing 15, e.g., via a coupling member.

Figure 3:
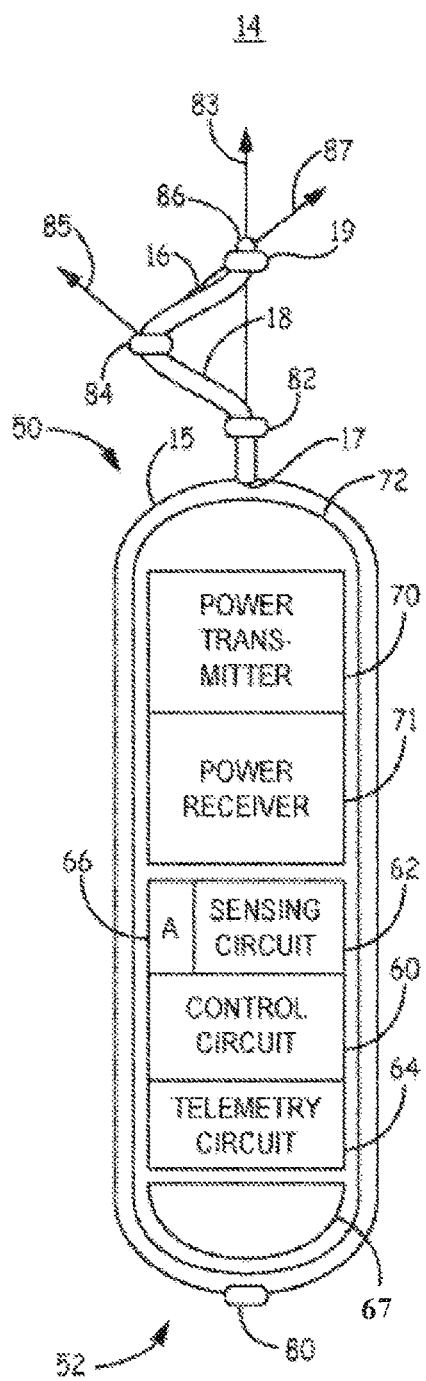
FIG. 3 is a schematic diagram of the sensing device of FIG. 1 according to one example.

For example, sensing device 14 and extension 16 may be implanted as a singular unit via an open incision at the desired implant site or advanced to and released at the implant site using a delivery tool such as a catheter or guide wire to enable a small incision and minimal invasiveness of the implant procedure. While sensing extension 16 is shown as a linear extension in the example of FIG. 1, another example of a non-linear sensing extension including one or more bends or curves is shown in FIG. 3.

System 10 may further include an external device 40 configured to transmit programming commands to sensing device 14 via wireless telemetry and receive data from sensing device 14. In some examples, sensing device 14 is a rechargeable device including one or more rechargeable batteries that are charged by external device 40. In such examples, external device 40 includes a power transmitter 46 including a regulated power source and a coil 48 for inductive power transfer via radio frequency (RF) coupling between primary coil 48 and a secondary coil included in sensing device 14. A power receiver in sensing device 14 receives the transmitted power and harvests at least a portion of the power for recharging the battery(ies). In some examples, a coil or transducer used for transmitting power from sensing device 14 to pulse delivery device 100 is also configured to receive power from external device 40.

Sensing device 14 is a programmable device including a telemetry circuit for sending and receiving data to external device 40. External device 40 is shown in telemetric communication with sensing device 14 by a communication link 42. External device 40 may include a processor; computer-readable storage media such as RAM, ROM, flash storage or other storage media; a display; a user interface; a telemetry unit 44 including a communication antenna or coil 45 for telemetric communication with sensing device 14 via communication link 42, and a power transmitter 46 including a primary coil 48 for transmitting RF energy to sensing device 14 at a selected resonant frequency separated from the communication frequency used by the telemetry unit antenna 45.

External device 40 communicates with sensing device 14 for transmitting and receiving data via communication link 42. Communication link 42 may be established between sensing device 14 and external device 40 using a radio frequency (RF) link such as BLUETOOTH®, Wi-Fi, or Medical Implant Communication Service (MICS) or other RF or communication frequency bandwidth.

External device 40 may be embodied as a programmer used in a hospital, clinic or physician's office to retrieve data from sensing device 14 and to program operating parameters and algorithms in sensing device 14 for controlling sensing and power transmission functions. External device 40 may be used to program cardiac event sensing parameters and power signal transmission control parameters used by sensing device 14 to control the timing and strength of power transmission to pulse delivery device 100, thereby controlling the timing and available energy for delivering pacing pulses by pulse delivery device 100.

Data stored or acquired by sensing device 14, including cardiac electrical signals, power transmission history, detected pacing pulses delivered by pulse delivery device 100, activity, posture, temperature, physiologic status, etc. or associated data derived therefrom, may be retrieved from sensing device 14 by external device 40 using an interrogation command. External device 40 may alternatively be embodied as a home monitor, bedside or hand-held device and used for recharging one or more batteries of sensing device 14, programming sensing device 14, and retrieving data from sensing device 14. Pulse delivery devices 100 and 102 may have no or limited communication capabilities in that they are passive devices configured only for harvesting power from ultrasound signals and delivering harvested power to pace the patient's heart 8.

Figure 2A:
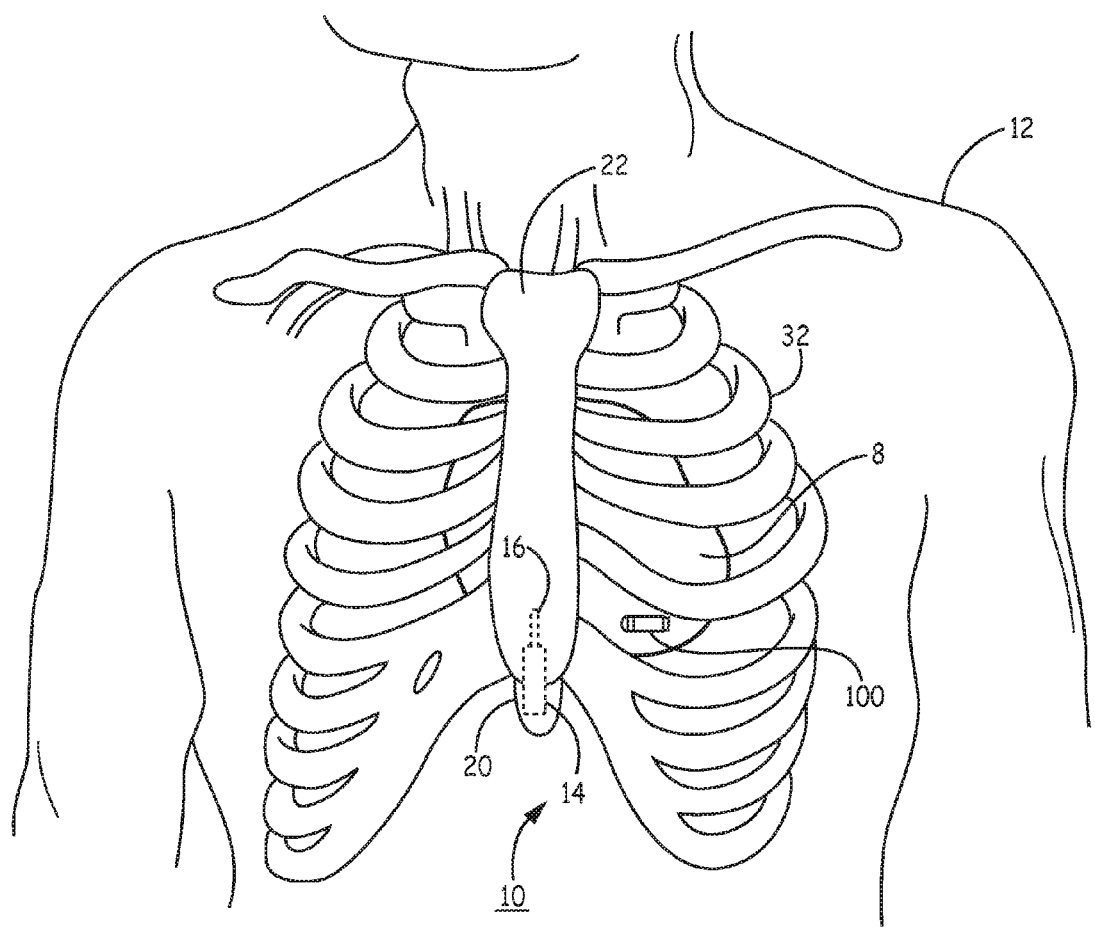
FIG. 2A is a front view and FIG. 2B is a side view of an implantable cardiac pacing system having a sensing device deployed at least partially substernally within a patient.
Figure 2B:
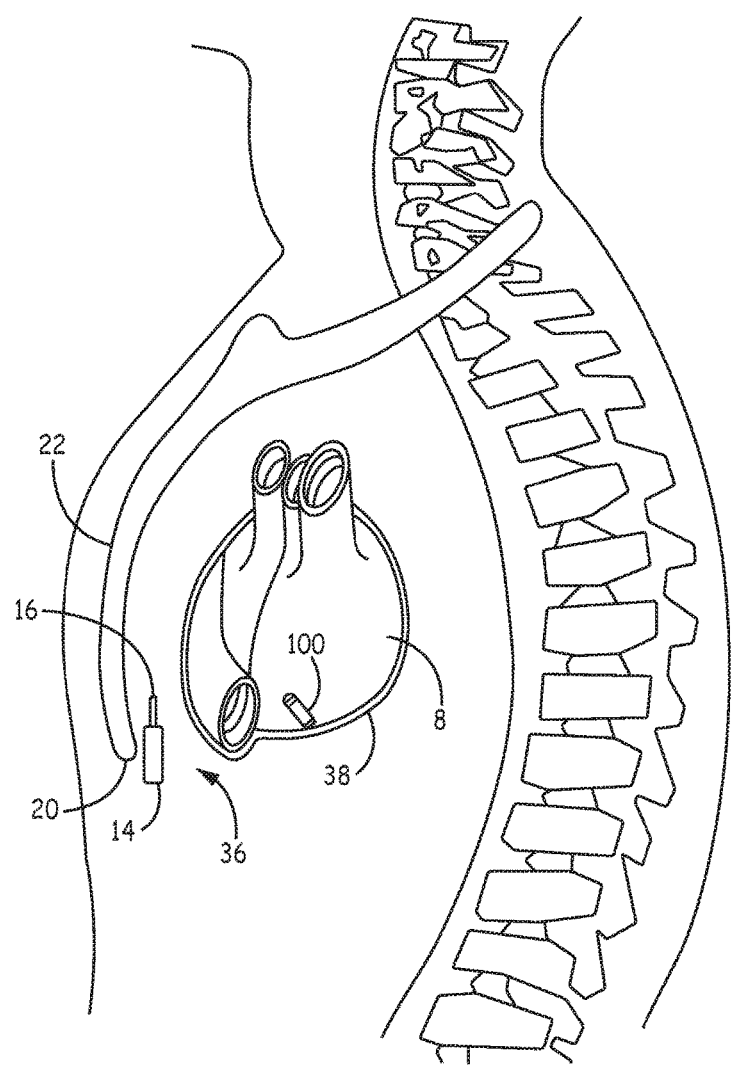

FIG. 2A is a front view of an implantable cardiac pacing system 10 in which sensing device 14 is shown implanted at least partially substernally within patient 12. FIG. 2B is a side view of sensing device 14 implanted substernally within patient 12. Pulse delivery device 100 is shown generally positioned along a ventricle of heart 8, e.g., along a cardiac vein, epicardially, within or along the pericardium 38, or endocardially within the right or left ventricle. Sensing device 14 may be implanted so that all or a portion of sensing extension 16 extends beneath sternum 22. Housing 15 of sensing device 14 may be positioned entirely beneath sternum 22, e.g., along the anterior mediastinum 36. In other examples, sensing device 14 may be implanted such that housing 15 is adjacent to or inferior to xiphoid process 20 with sensing extension extending superiorly beneath sternum 22.

Sensing device 14 is shown extending approximately parallel with sternum 22 but may extend in an at least a partially substernal position at an angle relative to sternum 22, e.g., with sensing extension 16 directed at an angle laterally to the left or the right of sternum 22. In other examples, sensing device 14 or at least a portion of sensing extension 16 may be implanted partially beneath ribcage 32.

FIG. 3 is a schematic diagram of sensing device 14 according to one example. Sensing device housing 15 encloses circuitry including a sensing circuit 62, a control circuit 60, and a telemetry circuit 64, all of which may be in the form of an integrated circuit coupled to a battery 67 for providing power to the components of the integrated circuit as needed. Battery 67 may include one or more rechargeable and/or non-rechargeable battery cells. In one example, battery 67 or another charge storage device is recharged via current induced on coil 72 via power transmitted by external device 40 (FIG. 1).

As described above, power may be transmitted to recharge battery 67 by RF coupling between a primary coil 48 included in external device 40 and secondary, induction coil 72 included in sensing device 14 for receiving power transmitted from external device 40 and charging battery 67 via power receiver 71. Secondary coil 72 may be additionally be coupled to telemetry circuit 64 to function as an antenna for communication telemetry with external device 40 depending on the communication telemetry frequency being used. Sensing device 14 may include a single coil 72 and decode circuitry to separate RF telemetry communication signals received from external device 40 from RF coupled power transmission from external device 40 for recharging battery 67.

Control circuit 60 may be configured to monitor the charge of battery 67 via a voltage line and transmit a signal via a transceiver included in telemetry circuit 64 to external device 40 to signal when a recharge of battery 67 is required. During recharging, control circuit 60 may monitor the battery charge and control telemetry circuit 64 to transmit a signal when battery 67 is fully charged, and recharging is complete. Control circuit 60 may include a thermistor or other temperature monitoring circuit component(s) for detecting an elevated temperature of the sensing device 14 during battery recharging. Control circuit 60 may control telemetry circuit 64 to transmit a signal to external device 40 to temporarily pause charging or reduce the charging rate to avoid overheating of sensing device 14 which could cause damage to components of sensing device 14 and/or local tissue heating. Examples of an implantable medical device with a rechargeable battery and associated recharging methods are generally disclosed in U.S. Pat. No. 8,909,351 (Dinsmoore, et al.) and U.S. Pat. No. 8,630,717 (Olson, et al.), both of which are incorporated herein by reference in their entirety.

Housing 15 also encloses a power transmitter circuit 70 for transmitting power to pulse delivery device 100. Power transmitter circuit 70 includes an array of ultrasound transducers, such as piezoelectric transducers, for transmitting power via acoustical signals, to pulse delivery device 100 (and 102 if present).

Housing 15 may be generally cylindrical or prismatic and may be formed of an electrically non-conductive material, such as a polymer, glass or ceramic that provides acceptable acoustical coupling from power transmitter 70 with the patient's tissue. In other examples, at least a portion of housing 15 may be formed of an electrically conductive material, e.g., a titanium alloy, stainless steel, or other biocompatible metal. In this case, secondary coil 72 may extend along a non-conductive portion of housing 15 or extend along an outer surface of housing 15 to promote efficient RF coupling between coil 72 and the external, primary coil 48. In some examples, housing 15 is formed from a special grade or alloy of titanium, such as Grade 5, Grade 23, or Ti 6AI-4V ELI alloy, which allows RF coupling through housing 15 to coil 72. Housing 15 may be coated or partially coated with a non-conductive coating such as parylene or other material.

In some examples, housing 15 may carry one or more housing-based electrodes 80. Sensing extension 16 is shown extending from housing distal end 50. An electrode 80 may be carried by the housing proximal end 52, as either an exposed circuit of an electrically conductive housing 15 or as a tip, button or ring electrode mounted along proximal housing end 52. Electrode 80 may be coupled to sensing circuit 62 via an electrical feedthrough or may be an electrically conductive portion of housing 15 serving as a ground or anode electrode. For example housing 15 may be formed of a titanium alloy with an insulating coating such as a parylene coating having an opening exposing electrode 80. In other examples, one or more exposed, electrically conductive portions of housing 15 may be provided as one or more housing-based electrodes that are selectable by sensing circuit 62 in any combination with the sensing extension electrodes 82, 84, and 86 to form a sensing electrode vector for acquiring cardiac electrical signals.

Sensing extension 16 includes an extension body 18 carrying three electrodes 82, 84, and 86 in the example shown. Electrodes 82, 84, and 86 may be ring electrodes, short coil electrodes, plate electrodes or the like. The distal-most electrode 86 may be a hemispherical tip electrode or a helical or hook type electrode providing fixation of sensing extension distal end 19. While three electrodes are shown along sensing extension 16, it is recognized that less than three or more than three electrodes may be carried by sensing extension 16.

Extension body 18 includes one or more lumens through which electrical conductors extend from a respective electrode 82, 84 or 86 to a respective electrical feedthrough extending across housing 15 and providing electrical connection to sensing circuit 82. In the example shown, a housing based electrode 80 is shown at the proximal end of housing 15. In other examples, one or more electrodes 82, 84 and 86 may be coupled to housing 15 when formed of an electrically conductive material and serve as a return anode or ground in the electrical sensing vector without requiring an electrical feedthrough at the distal end of housing 15.

Sensing circuit 62 may include switching circuitry for selecting a sensing electrode vector from among the available electrodes 80, 82, 84, and 86. Switching circuitry may include a switch array, switch matrix, multiplexer, or any other type of switching device suitable to selectively couple the selected electrodes to a sense amplifier or other cardiac event detection circuitry included in sensing circuit 62. Sensing circuit 62 may include one or more sensing channels to enable monitoring of one or more cardiac electrical signals simultaneously. Each sensing channel may include an input filter and preamplifier for receiving a cardiac electrical signal via the selected sensing electrode vector, a sense amplifier or other cardiac event detector for sensing cardiac events such as P-waves or R-waves, e.g., based on an auto-adjusting threshold crossing of the cardiac electrical signal.

Sensing extension body 18 is shown having a preformed shape including multiple bends or curves so that electrodes 82, 84 and 86 are positioned along different sensing vectors. For example, sensing circuit 62 may be selectively coupled to electrodes 82 and 86 for sensing a cardiac electrical signal along vector 83. Alternatively, sensing circuit 62 may be selectively coupled to electrodes 82 and 84 for sensing a cardiac electrical signal along vector 85. In yet another example, electrodes 84 and 86 may be selected for sensing along vector 87. Sensing extension body 18 may curve in approximately a sine wave or "C" shape and may curve or bend in two or three dimensions in order to position electrodes 82, 84 and 86 along at least two different sensing vectors, which may be three orthogonal sensing vectors. The resulting sensing vectors used when housing-based electrode 80 is selected with sensing extension-based electrode 84 is along a different vector than vectors 83, 85 or 87 providing a fourth possible sensing vector. Different electrode spacing and different sensing vectors allow for an optimal sensing electrode combination to be selected for sensing a cardiac electrical signal and identifying cardiac events, e.g., P-waves and R-waves.

Sensing circuit 62 may pass a cardiac sensed event signal to control circuit 60 upon sensing a cardiac event, such as a P-wave sensed event signal or an R-wave sensed event signal. Sensing circuit 62 may additionally include an analog-to-digital converter for providing a digitized ECG signal to control circuit 60 for performing morphology analysis or other event detection algorithms for detecting and identifying P-waves and R-waves from the cardiac electrical signal.

Sensing circuit 62 may further be configured to detect pulses delivered by pulse delivery device 100. Detection of pulses delivered by pulse delivery device 100 may be used for feedback in controlling the power transmitted by sensing device 14 and the timing of the power transmission. In some examples, sensing circuit 62 may be configured to detect an evoked response for confirming cardiac capture by delivered pulses such that power being transmitted may be adjusted up or down as needed to promote a high likelihood of capture at a minimum pacing pulse energy to maximize battery longevity of sensing device 14.

In some cases, sensing circuit 62 is configured to detect pulses delivered by pulse delivery device 100 when power transmitter 72 is transmitting a power transmission signal, e.g., an ultrasound signal, in a series of multiple, different directions. Power transmitter 72 may be controlled by control circuit 60 to transmit an ultrasound signal in multiple directions. The ultrasound signal may intentionally be transmitted at a low amplitude so that the power received by pulse delivery device 100 is too low to produce a pulse having an amplitude greater than the cardiac capture threshold, also referred to as a sub-threshold pacing pulse. The pulse delivery device 100 harvests power from the received ultrasound signal and delivers a sub-threshold pacing pulse for each power transmission in the series. Sensing circuit 62 senses the delivered pulses and may provide control circuit 62 with a peak amplitude of the pulse produced for each directional ultrasound signal so that control circuit 62 may determine which direction is optimal for transmitting power to pulse delivery device 100.

For example, if a series of ultrasound signals is transmitted in three to five different directions through control of an ultrasound transducer array included in power transmitter 70, the transmitted signal resulting in the highest pulse delivered by pulse delivery device 100 is identified as being the optimal direction for power transmission. In this way, sensing device 14 is enabled to target the location of pulse delivery device 100 for power transmission. When multiple pulse delivery devices 100 and 102 are present, the targeted directionality for optimal power transmission can be determined for each pulse delivery device. By sending out several "targeting" signals in various directions and sensing the resulting voltage produced by the pulse delivery device 100, sensing device 14 can discern the direction of the pulse delivery device 100 from the sensing device 14, and thus the desired directionality of the power transmission signal. The same electrodes 80, 82, 84 and 86 and circuitry of sensing circuit 62 used for sensing cardiac electrical signals may be used for detecting delivered pulses to enable determination of the delivered pulse amplitudes and selecting directionality of the power transmission signal.

Control circuit 60 may include a microprocessor and computer-readable memory or other storage media for implementing and executing software and firmware programs for performing the functions attributed to sensing device 14 herein. The circuits included in sensing device 14 may include on or more of an application specific integrated circuit (ASIC), an electronic circuit, a processor (shared, dedicated, or group) and memory that execute one or more software or firmware programs, a combinational logic circuit, state machine, switching circuitry, or other suitable components that provide the described functionality attributed to sensing device 14. The particular form of software, hardware and/or firmware employed to implement the functionality disclosed herein will be determined primarily by the particular system architecture employed in sensing device 14. Providing software, hardware, and/or firmware to accomplish the described functionality in the context of any modern implantable medical device system, given the disclosure herein, is within the abilities of one of skill in the art.

Control circuit 60 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, control circuit 60 may include non-transitory computer readable media storing instructions that, when executed by one or more processing circuits, cause control circuit 60, in combination with sensing circuit 62, telemetry circuit 64 and power transmitter 70 to perform various functions attributed to sensing device 14. The non-transitory, computer-readable media storing the instructions may include any of the media listed above.

Control circuit 60 is configured to receive cardiac electrical signals from sensing circuit 62 for identifying P-waves and R-waves. Signals received from sensing circuit 62 may be a logic signal, referred to herein as P-wave sensed event signal indicating the timing of a sensed P-wave, e.g., based on a P-wave sensing threshold crossing of the cardiac electrical signal, or an R-wave sensed event signal, e.g., based on an R-wave sensing threshold crossing of the cardiac electrical signal. Signals received from sensing circuit 62 may be a digital ECG signal received for additional signal analysis for identifying P-waves and/or R-waves.

Control circuit 60 is configured to identify cardiac events, e.g., P-waves and R-waves for determining a pacing interval, set the pacing interval in response identifying a P-wave or R-wave, depending on a programmed pacing mode, and enable power transmitter 70 to transmit power to pulse delivery device 100 upon expiration of the pacing interval. As such, control circuit 60 may include a pacing interval timer or counter for determining the expiration of the pacing interval started upon an identified cardiac event. The power may be transmitted for a time duration of a desired pacing pulse delivered by pulse delivery device 100 such that the transmitted power is harvested and delivered as a pacing pulse by pulse delivery device 100 without requiring a battery or active, independent charge storage device in pulse delivery device 100. As such, control circuit 60 may additionally include a pulse duration timer or counter for controlling the duration of time that the power transmitter 70 is enabled to transmit power. In this way, sensing device 14 controls the timing and duration of the pacing pulse delivered by pulse delivery device 100, but sensing device 14 does not deliver electrical stimulation pulses directly to the heart (or other body tissue) and therefore does not require a pacing pulse generator coupled to pacing electrodes. Power transmitter 70 produces acoustic power transmission signals by delivering a drive signal, under the control of control circuit 60, to an array of ultrasound transducers included in power transmitter 70. Control circuit 60, sensing circuit 62, and/or power transmitter 70 may include protection circuitry to prevent damage from defibrillation energy delivered to patient 12 by another device and to block conduction during such events. An arrangement of system 10 incorporating acoustic power transmission is described below in conjunction with FIG. 4.

In some examples, sensing device 14 includes a patient activity sensor 66, which may be implemented as an accelerometer, for sensing patient activity. An accelerometer and associated method for determining a sensor-indicated pacing rate for supporting the patient's metabolic demand is generally disclosed in U.S. Pat. No. 7,031,772 (Condie, et al.), incorporated herein by reference in its entirety. Activity sensor 66 may be a piezoelectric transducer or a MEMS device bonded to an inner surface of housing 15 or incorporated on an internal substrate of an integrated circuit carrying sensing circuit 62, control circuit 60 and telemetry circuit 64. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers used for sensing patient activity and posture are generally described in U.S. Pat. No. 5,593,431 (Sheldon), and U.S. Pat. No. 6,044,297 (Sheldon), both of which are incorporated herein by reference in their entirety.

Control circuit 60 may be configured to determine an activity count from a signal received from activity sensor 66. The activity count is correlated to the level of patient activity. The activity count is converted to a sensor-indicated pacing rate using a transfer function or look-up table stored in memory included in control circuit 60 relating activity counts to pacing rate. A pacing rate interval may then be determined based on the sensor-indicated pacing rate. Control circuit 60 may be configured to identify P-waves and set a pacing interval for controlling pulse delivery device 100 to deliver a ventricular pacing pulse synchronized to the P-wave at a desired atrioventricular (AV) interval. However, when P-waves cannot be identified, or when control circuit 60 detects atrial fibrillation according to an implemented tachyarrhythmia detection algorithm, sensing device 14 may switch from an atrial synchronous mode of controlling ventricular pacing to a non-synchronized, single chamber rate-responsive pacing mode.

Telemetry circuit 64 may include a transceiver and antenna for transmitting and receiving radio frequency or other communication frequency signals to and from external device 40 as described above. The telemetry antenna may be included in housing 15 or external to housing 15. In some examples, coil 72 may have a dual function as a telemetry communication antenna and a power receiving coil for recharging battery 67. An example of an implantable medical device system having switchable inductive energy transfer and communication telemetry between external and implanted coils is generally disclosed in U.S. Pat. No. 8,265,770 (Toy, et al.), incorporated herein by reference in its entirety. Another example of a system for communicating with and providing power to an implantable stimulator that includes aspects that may be implemented in system 10 is generally disclosed in U.S. Pat. No. 8,386,048 (McClure, et al.), also incorporated herein by reference in its entirety. Control circuit 60 may be programmable such that operating parameters, such as sensing electrode vector, sensing thresholds, sensitivity, pacing intervals, parameters used to automatically determine pacing intervals, and power transmission control parameters, are programmable by a user using external device 40.

Figure 4:
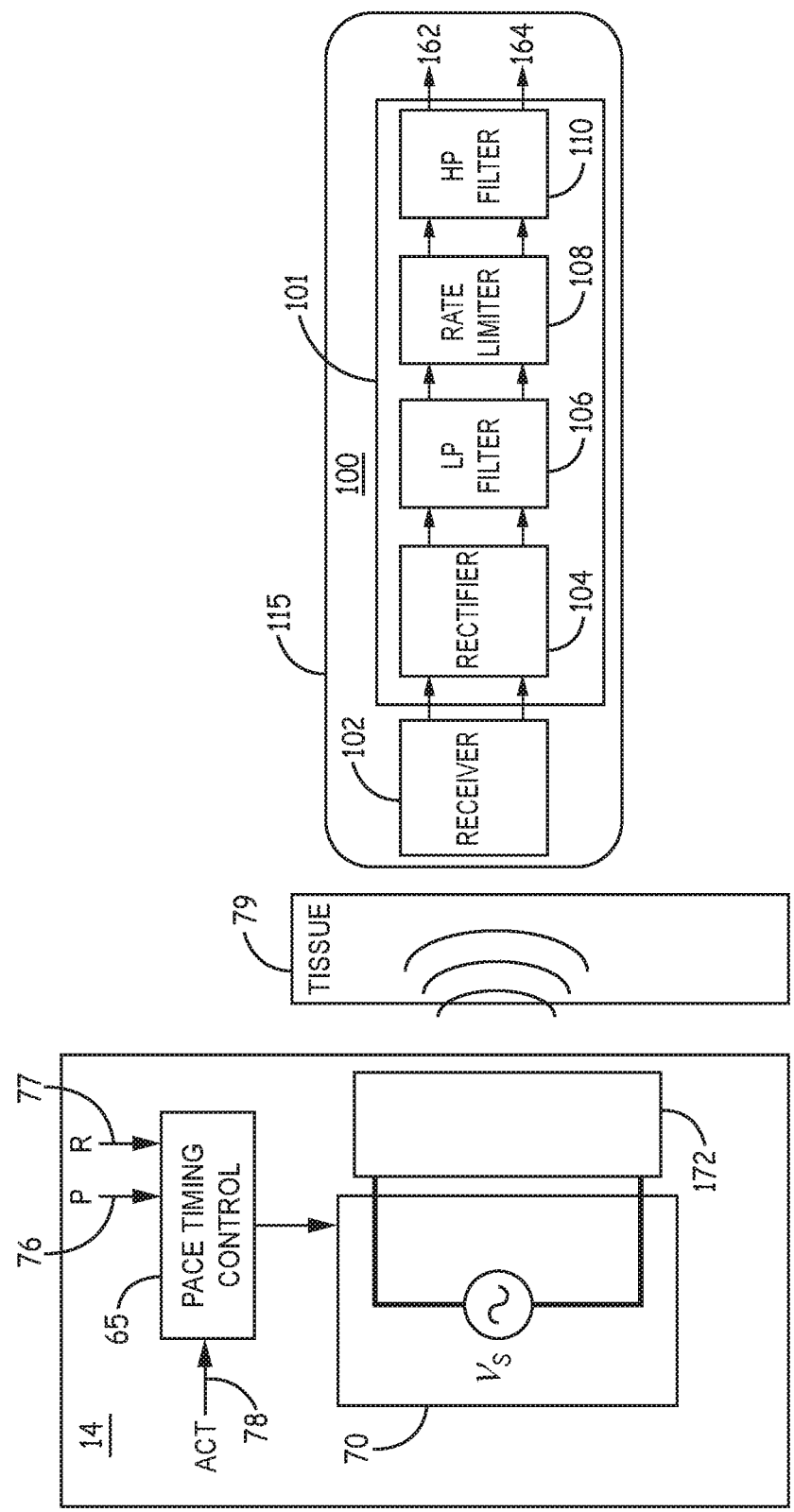
FIG. 4 is a conceptual diagram of an arrangement of the implantable medical device system of FIG. 1.

FIG. 4 is a conceptual diagram of an arrangement of sensing device 14 and pulse delivery device 100. Power transmitter 70 of sensing device 14 applies a drive signal to an array of ultrasound transducers 172 configured to transmit ultrasound through body tissue 79 directed to a receiver 102 included in pulse delivery device 100. Power transmitter 70 in this example may include an ultrasound oscillator operating in the range of 500 kHz to 10 MHz for example, voltage amplifiers to produce a signal on the order of tens of volts, and phase adjustment circuitry for adjusting the phase of the signal applied to each element of the transducer array.

Upon receipt of a sensed event signal 76 or 77, pace timing and control circuit 65 sets a corresponding pacing interval, e.g., an AV interval or a ventricular pacing rate interval, and controls power transmitter 70 to apply a drive signal to an array of ultrasound transducers 172 to transmit acoustical power upon expiration of the pacing interval. A new pacing interval may be set in response to expiration of the pacing interval and if a subsequent P-wave sensed event signal 76 or subsequent R-wave sensed event signal 77 is not received by pace timing control 65 during the pacing interval, power transmitter 70 is again enabled to transmit power to pulse delivery device 100 for the next pacing pulse.

In the absence of identifiable P-waves, or the detection of an atrial tachyarrhythmia, pace timing control circuit 65 may switch to activity-based pacing by setting a pacing rate interval based on a sensor-indicated pacing rate determined using an activity count signal 78 determined from activity sensor 66 (FIG. 3). Pace timing and control circuit 65 controls the starting time and ending time of acoustical power transmission and thereby controls the time a pacing pulse is delivered by pulse delivery device 100 as well as the duration of the pacing pulse.

Circuitry included in pulse delivery device 100 may include a rate limiting, filtering circuit 101 and an acoustical receiver 102 coupled to the circuit 101. Housing 115 of pulse delivery device 100 encloses the circuit 101 and acoustical receiver 102 and may include an acoustic coupling member as generally disclosed in U.S. patent application Ser. No. 14/694,990 (O'Brien, et al.) to promote efficient coupling of acoustical energy transmitted from sensing device 14 to pulse delivery device 100. U.S. patent application Ser. No. 14/694,990 is incorporated herein by reference in its entirety.

Acoustical receiver 102 includes a piezoelectric element, or an array of piezoelectric elements, responsive to the ultrasound transmission frequency transmitted by sensing device 14. For example acoustical receiver 102 may generate electrical charge in response to ultrasound energy transmitted at approximately 1 MHz. The piezoelectric element(s) may include a ceramic or crystal material that accumulates electrical charge in response to ultrasound energy transmitted through the patient's body. In some instances, the ultrasound energy may include diagnostic ultrasound energy applied to the patient for diagnostic purposes. The diagnostic ultrasound energy may be applied at frequencies that the piezoelectric material included in acoustical receiver 102 is responsive to. As such, acoustical receiver 102 may produce voltage signals in response to receiving ultrasound energy transmitted through the patient's body tissue 79 that includes ultrasound signals transmitted by sensing device 14 and diagnostic ultrasound signals transmitted by other sources.

Circuit 101 is configured to pass at least a portion of the voltage signals produced by acoustical receiver 102 to electrodes 162 and 164 for delivering electrical stimulation pulses to the patient's heart 8 and block voltage signals produced by the acoustical receiver 102 at an interval less than a maximum pacing pulse rate interval after a preceding voltage signal is passed to electrodes 162 and 164 as a pacing pulse. Voltage signals produced by acoustical receiver in response to ultrasound energy transmitted by sensing device 14 are passed to electrodes 162 and 164. Voltage signals produced by acoustical receiver 102 in response to diagnostic ultrasound energy transmitted through the patient's body are blocked from being passed to electrodes 162 and 164, e.g., by filtering the voltage signals and/or shunting current in the circuit 101 away from electrodes 162 and 164.

Circuit 101 is shown to include a rectifier 104, low pass filter 106, rate limiter 108, and high pass filter 110, all enclosed by housing 115. Low pass filter 106, rate limiter 108 and high pass filter 110 are provided for filtering acoustical energy received by receiver 102 from sources other than sensing device 14. Rectifier 104 receives the AC signal, e.g., the 1 MHz AC signal, produced by receiver 102 in response to ultrasound signals transmitted through the patient's body and converts the AC signal to DC. Rectifier 104 passes voltage signals produced by the acoustical receiver 102 to low pass filter 106 and rate limiter 108 as rectified voltage signals. Circuit 101 may include a voltage limiter, which may be implemented as diodes included in rectifier 104, for example. The voltage limiter limits a maximum voltage of the voltage signals that are passed to the pair of electrodes 162 and 164 and protects of the circuitry of pulse delivery device 100 from high voltages that might otherwise be generated by high intensity ultrasound.

Low pass filter 106 filters the voltage signals produced by acoustical receiver in response to short duration diagnostic ultrasound pulses that are shorter than a minimum pacing pulse duration, e.g., short pulses of ultrasound energy that have a pulse duration less than 100 microseconds. In some examples, rectified voltage pulses received by low pass filter 106 that are 10 microseconds or less in duration are filtered.

Rate limiter 108 may be provided for blocking diagnostic ultrasound bursts occurring at short intervals that are less than a maximum pacing rate interval, e.g., less than 300 ms, from being passed to electrodes 162 and 164. High rate pulses caused by bursts of diagnostic ultrasound pulsed could otherwise potentially result in an undesirably fast pacing rate. Rate limiter 108 may include a shunt configured to shunt a voltage signal produced by the piezoelectric element(s) of acoustical receiver 102 away from the electrodes 162 and 164 if the voltage signals produced by the piezoelectric element(s) occur at a rate that is higher than a maximum pulse delivery rate, e.g., faster than a maximum cardiac pacing rate which may be 100 pulses per minute, 120 pulses per minute, 140 pulses per minute or other specified maximum rate.

High pass filter 110 may be provided for filtering long duration diagnostic ultrasound bursts, e.g., bursts longer than 10 ms, which could otherwise potentially result in a sustained DC current delivered to the heart by the passive pulse delivery device 100. Sustained DC pulses may be arrhythmogenic. High pass filter 110 is coupled to the rate limiter 108 and may be configured to pass a voltage signal received from the rate limiter 108 having a pulse duration up to a maximum pacing pulse duration to the pair of electrodes 162 and 164. Circuit 101 may include a shunt configured to shunt a voltage signal produced by the piezoelectric element(s) of acoustical receiver 102 away from the electrodes 162 and 164 if the voltage signal produced by the piezoelectric element(s) is longer than a maximum electrical stimulation pulse duration.

Ultrasound energy received by acoustical receiver 102 that is rectified and passed by low pass filter 106, rate limiter 108 and high pass filter 110 is delivered to the patient's heart by pacing electrodes 162 and 164. Electrodes 162 and 164 are an anode and cathode pair which may be in the form of a ring electrode and tip electrode respectively as described in conjunction with FIG. 1. Circuit 101 coupled to one or more piezoelectric elements included in acoustical receiver 102 is thus configured to deliver electrical stimulation pulses to the patient's body by passing voltage signals produced by the piezoelectric element(s) of acoustical receiver 102 in response to the ultrasound signals transmitted sensing device 14 to electrodes 162 and 164 and block voltage signals from being passed to electrodes 162 and 164 that are produced by the piezoelectric element(s) of acoustical receiver 102 in response to diagnostic ultrasound signals.

Circuit 101 includes a low pass filter configured to filter voltage signals produced by the piezoelectric element(s) in response to receiving diagnostic ultrasound pulses having a pulse duration less than a minimum electrical stimulation pulse duration and a high pass filter configured to filter voltage signals produced by the piezoelectric element(s) in response to receiving diagnostic ultrasound bursts having a pulse duration greater than a maximum electrical stimulation pulse duration. Circuit 101 includes a rate limiter including a shunt configured to shunt current in the circuit 101 away from electrodes 162 and 164 in response to voltage signals produced by the piezoelectric element(s) upon receiving diagnostic ultrasound signals at a rate that is greater than a maximum pacing pulse rate (or other maximum electrical stimulation pulse delivery rate).

Figure 5:
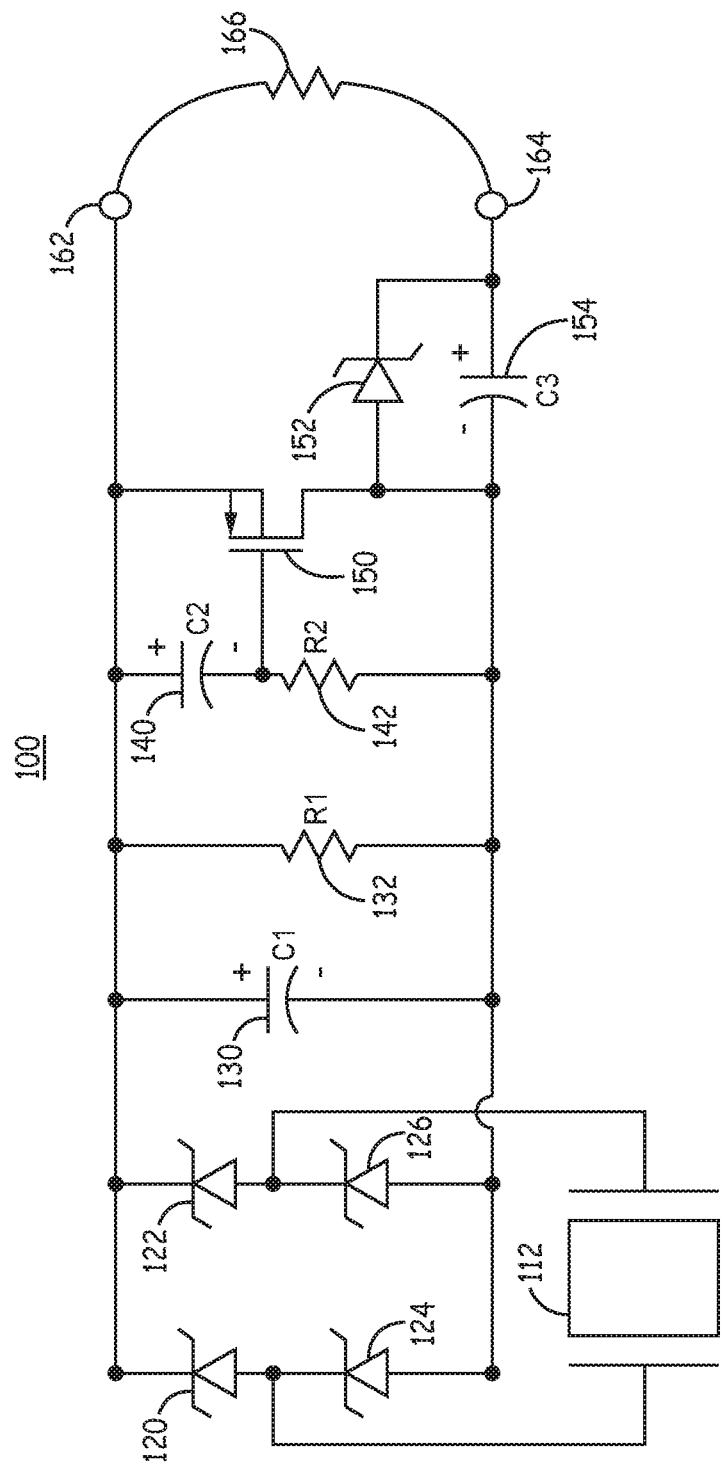
FIG. 5 is a schematic diagram of circuitry that may be included in the pulse delivery device of FIG. 1 according to one example.

FIG. 5 is a schematic diagram of circuitry that may be included in pulse delivery device 100 according to one example. The acoustical receiver 102 of FIG. 4 may be implemented as a piezoelectric element 112 that generates charge and acts like a voltage source in series with a capacitor when subjected to ultrasound energy. Piezoelectric element 112 may be a single piezoelectric element or multiple elements arranged in series and/or parallel. When not receiving ultrasound energy, piezoelectric element 112 does not generate charge, and pulse delivery device 100 is wholly inactive because no other on-board independent power source is provided. All components included in pulse delivery device 100 are passive components such that a pacing pulse is delivered across electrodes 164 and 162 of pulse delivery device 100 only when piezoelectric element 102 is receiving ultrasound energy. Otherwise pulse delivery device 100 is inactive.

In the example of FIG. 5, the rectifier 104 of FIG. 4 includes four Zener diodes 120, 122, 124 and 126. Zener diodes 120, 122, 124 and 126 may be 10 V Zener diodes, for instance, and may limit the voltage received from piezoelectric element 112 to a maximum available pacing pulse voltage amplitude according to the Zener voltage. Zener diodes 120, 122, 124 and 126 provide both rectification and voltage limiting of the signal produced by piezoelectric element 112. Capacitor C1 130 filters short duration pulses of the rectified signal that would be associated with short diagnostic ultrasound bursts, e.g., up to 10 microsecond bursts of a 1 MHz carrier frequency. Capacitor C1 130 may correspond to low pass filter 106 of FIG. 4.

Capacitor C2 140 and resistor R2 142 are provided with an RC time constant that is relatively long compared to the maximum desired pacing pulse duration. For example, if pacing pulses are delivered with a pulse duration of 0.1 to 2 ms, the RC time constant of capacitor C2 140 and resistor R2 140 may be at least five to ten times longer. Capacitor C2 charges in response to long duration pulses produced by piezoelectric element 112 when subjected to ultrasound bursts from sources other than sensing device 14 that are longer than the maximum pacing pulse width. MOSFET gate 150 shunts away current from capacitor C2 140 so that capacitor C2 can be recharged for the next pulse. In this way, R2 142, C2 140 and MOSFET gate 150 act as a rate limiter, and generally correspond to rate limiter 108 of FIG. 4, by filtering and shunting away energy from long duration diagnostic ultrasound pulses delivered at a rapid rate. For example, diagnostic ultrasound bursts may be delivered for 0.1 to 10 ms repeated at a short interval, e.g., less than 300 ms. If not filtered by pulse delivery device 100, these long duration, rapidly delivered diagnostic ultrasound pulses may lead to high rate, high energy ventricular pacing which is generally undesirable.

Capacitor C3 154 is a DC blocking capacitor that prevents a long duration pulse from being delivered to the cathode electrode 164. Once capacitor C3 154 is fully charged, it discharges through the cathode electrode 164, pacing load 166 and return anode electrode 162 and through resistor R1 132. The RC time constant of resistor R1 132 and capacitor C3 154 is relatively shorter than the pacing rate interval. For example, pacing rate intervals may range from 2 seconds to 400 ms (corresponding to pacing rates of 30 pulses per minute to as high as 150 pulses per minute). The RC time constant of R1 132 and C3 154 may be less than 200 ms, between 100 and 200 ms, or less than 100 ms, for instance. Capacitor C3 154 charges when piezoelectric element is receiving ultrasound energy that is not filtered by C1 (very short duration ultrasound pulses) or by MOSFET 150 (rapid ultrasound pulses), and discharges quickly so that it is ready to be recharged when piezoelectric element 112 receives the next ultrasound pulse transmitted by sensing device 14 at the expiration of the next pacing pulse interval.

The time constant of capacitor C3 and the pacing load 166 may be on the order of 1 ms. When the sensing device 14 transmits ultrasound energy for a desired pulse duration, e.g., approximately 0.25 ms, capacitor C3 154 charges, for example up to about 25% of the maximum pacing pulse amplitude if the energy is transmitted for 0.25 ms, then discharges through the pacing load 166 with a time constant determined by capacitor C1 130 and pacing load 166. The pacing pulse may be a rectangular pulse that decays from the starting pulse amplitude as capacitor C3 154 is discharged. At the end of the ultrasound pulse transmitted by sensing device 14, the potential difference between the cathode electrode 164 and anode electrode 162 is equalized through the pacing load 166 according to a time constant defined by capacitor C1 130 and the pacing load 166, which may be on the order of 10 microseconds to 100 microseconds, so that the rectangular pacing pulse waveform terminates quickly upon termination of the ultrasound pulse transmitted by sensing device 14.

Output capacitor C3 154 acts as a high pass filter (e.g., included in high pass filter 110 of FIG. 4) that blocks DC currents but passes narrow pulses, e.g., pulses up to 0.5 ms or other maximum pacing pulse duration, that are not filtered by low pass filter capacitor C1 130 or by the rate limiting function of capacitor C2 140 and MOSFET 150. The narrow pulses are passed to electrodes 164 and 162 to capture and pace the heart. Remaining charge on output capacitor C3 154 is quickly discharged through R1 132 after the pacing pulse is complete, when the potential difference across the pacing load 166 is zero and current stops flowing through the pacing load 166. Diode 152 is provided in parallel to output capacitor C3 154 in this example to protect capacitor C3 154 from damage due to electrical energy that may be applied to the patient, such as electrocautery or defibrillation shocks.

Figure 6:
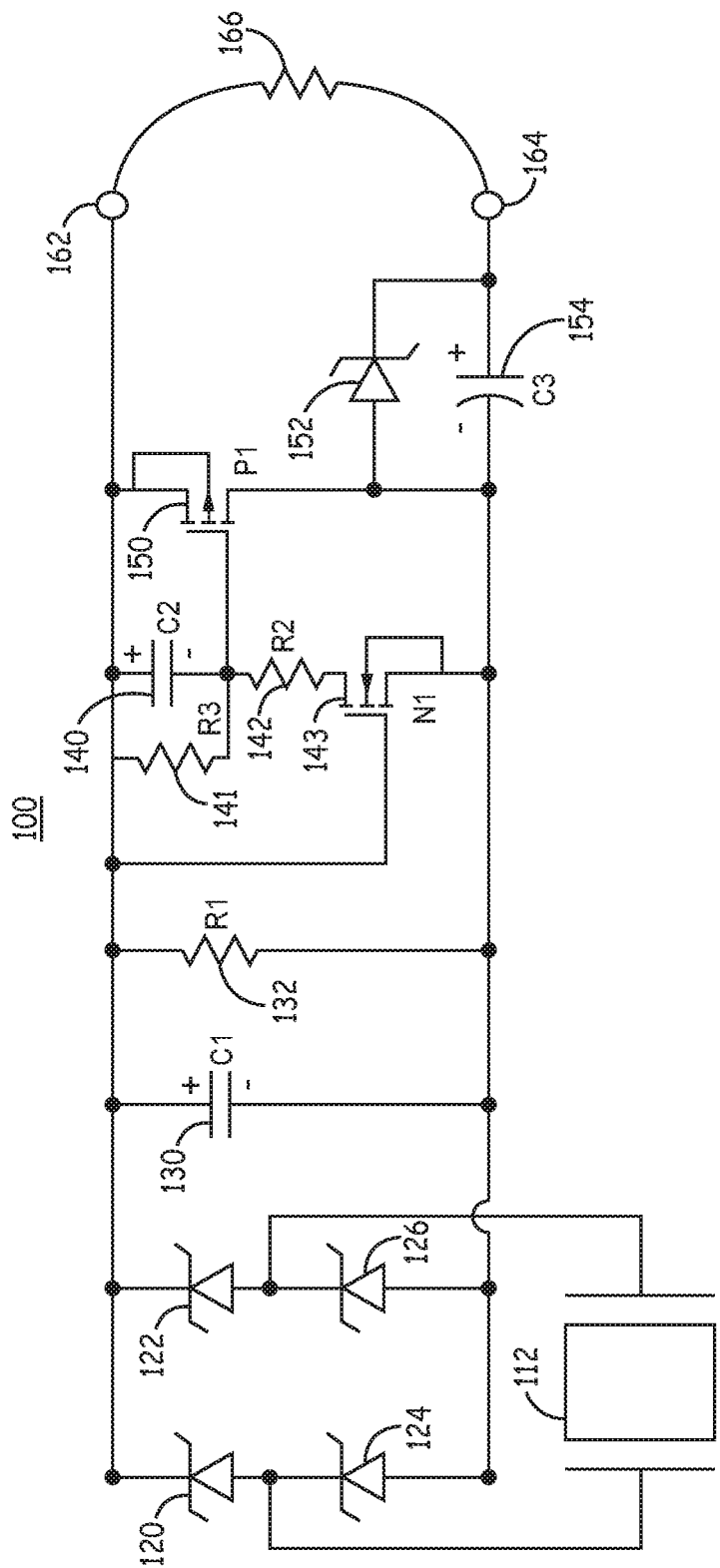
FIG. 6 is a schematic diagram of circuitry that may be included in the pulse delivery device of FIG. 1 according to another example.

FIG. 6 is a schematic diagram of circuitry that may be included in the pulse delivery device 100 of FIG. 1 according to another example. As described in conjunction with FIG. 5, the pulse delivery device 100 may include a piezoelectric receiver 112 that produces a voltage signal in response to acoustical energy transmitted through the patient's body, e.g. at about 1 MHz or other selected frequency of frequency range. A rectifier, implemented using Zener diodes 120, 122, 124 and 126 in the examples of FIG. 5 and FIG. 6, converts the 1 MHz signal to a rectified, DC signal having a negative polarity and may limit the maximum negative voltage of the DC signal that is passed to a low pass filter, implemented as capacitor C1 130 for filtering short duration diagnostic ultrasound pulses that may be applied to the patient.

Capacitor C1 130 may be a 20 nanofarad capacitor in one example. If a 1 mA signal is passed from the rectifier embodied as Zener diodes 120-126, a 1 Volt pacing pulse would be delivered across electrodes 162 and 164 through a pacing load 166 of 1,000 ohms, for instance, without filtering by capacitor C1 130. However, if the pulse is less than 5 microseconds, the pulse amplitude is limited to less than 0.25 V, a four-fold reduction, and will have a pulse energy that is insufficient to effectively pace and capture the heart.

In the example of FIG. 6, the components corresponding to rate limiter 108 of FIG. 4 may include a peak detector for detecting peaks of the rectified signal. For instance, rate limiter may include capacitor C2 140, resistor R2 142, and MOSFET P1 150 as described above, and in this example MOSFET N1 143 may be provided as a negative peak detector that passes peak signals in the rectified signal that exceed a threshold to resistor R2 142. Peak signals passed through resistor R2 142 charge capacitor C2 140 to the negative peak voltage of the rectified signal when it exceeds the threshold of the negative peak detector, e.g., exceeding a threshold of −0.25 to −0.5 V threshold. Resistor R2 142 and capacitor C2 140 may be provided with a time constant on the order of ten times larger than a typical pacing pulse duration to prevent shunting current of a voltage signal produced by piezoelectric element 112 in response to an ultrasound signal transmitted by sensing device 14 having the intended pacing pulse width. For example, if the pacing pulse width is intended to be approximately 0.25 ms, the time constant of resistor R2 142 and capacitor C2 140 may be approximately 2.5 ms. Resistor R2 142 may be relatively high compared to the pacing load 166 to reduce energy losses. For instance, a typical pacing load 166 may be on the order of 1000 ohms, resistor R2 142 may be provided as a 100 Kohm resistor and capacitor C2 140 may be provided as a 25 nanofarad capacitor.

In one example, MOSFET N1 143 detects a negative, rectified voltage exceeding approximately −0.4 V relative to anode electrode 162. If the threshold of MOSFET N1 is too low, current leaking to capacitor C2 140 may cause capacitor C2 140 to discharge too quickly making the rate limiter of the circuit less effective in filtering high rate diagnostic ultrasound pulses.

MOSFET P1 150 turns on when the negative peak voltage across C2 140 exceeds the threshold voltage (e.g., −0.25 to −0.5 V) so that diagnostic ultrasound pulses occurring at short intervals that are less than a minimum pacing rate interval are shunted by capacitor C2 discharging through resistor R3 141. The threshold voltage of MOSFET P1 150 may be between 0.2 and 0.5V to effectively shunt pulses occurring at high rates that are greater than approximately 0.25 Volts or greater than 0.5 V. If the threshold voltage of MOSFET P1 150 is too low, current leakage through MOSFET P1 150 may reduce the efficiency of delivering pacing pulses.

Resistor R3 141 is provided with a high resistance so that the time constant of resistor R3 141 and capacitor C2 140 is less than the minimum expected pacing rate interval, for example less than 300 ms, less than 400 ms or less than 500 ms. For instance, resistor R3 141 may have a resistance on the order of 10 to 20 megaohms. A relatively high resistance of resistor R3 141 improves the filtering of high rate ultrasound pulses by circuit 101.

After the pulses at short intervals stop, capacitor C2 is discharged and longer pulses occurring at longer intervals may be passed to capacitor C3 154, thereby providing a rate limit of pulses passed to the pacing electrodes 162 and 164. The rate limiter of FIG. 6 including MOSFET N1 143 allows peak signals of ultrasound bursts being received at a rapid pulse rate to be shunted away from electrodes 162 and 164 rather than an average of short interval bursts of ultrasound pulses as in the rate limiter of FIG. 5.

As described above, capacitor C3 154 passes pulses having a pulse duration up to a maximum pacing pulse width but blocks DC current and limits the pulse width of long duration pulses. Resistor R1 132 shunts away accumulated charge from capacitor C3 154 after the pacing pulse is complete to prepare the circuit for the next pacing pulse by discharging capacitor C3 154 during a single charge/discharge cycle which produces a single cardiac pacing pulse delivered by electrodes 162 and 164 across the pacing impedance load 166. Capacitor C3 may be provided with a capacitance of approximately 2 microfarads to filter long pulses and minimize energy lost for delivering pacing pulses having a pulse width of approximately 0.25 ms, for example. Resistor R1 132 may be provided with a resistance approximately 50 times larger than the expected pacing load 166 to discharge capacitor C3 154 before the next pacing pulse and minimize energy losses during pacing pulse delivery. Resistor R1 132 may be approximately 50 Kohms in one example.

The values of the various components of the circuits shown in FIGS. 5 and 6 are provided as examples with no limitation intended. It is recognized that the particular components and component values may vary between embodiments and may be selected according to an expected range of pacing pulse rate, pacing pulse width, pacing pulse amplitude and pacing load anticipated while attempting to minimize energy losses of the circuit to maximize pacing efficiency.

Figure 7:
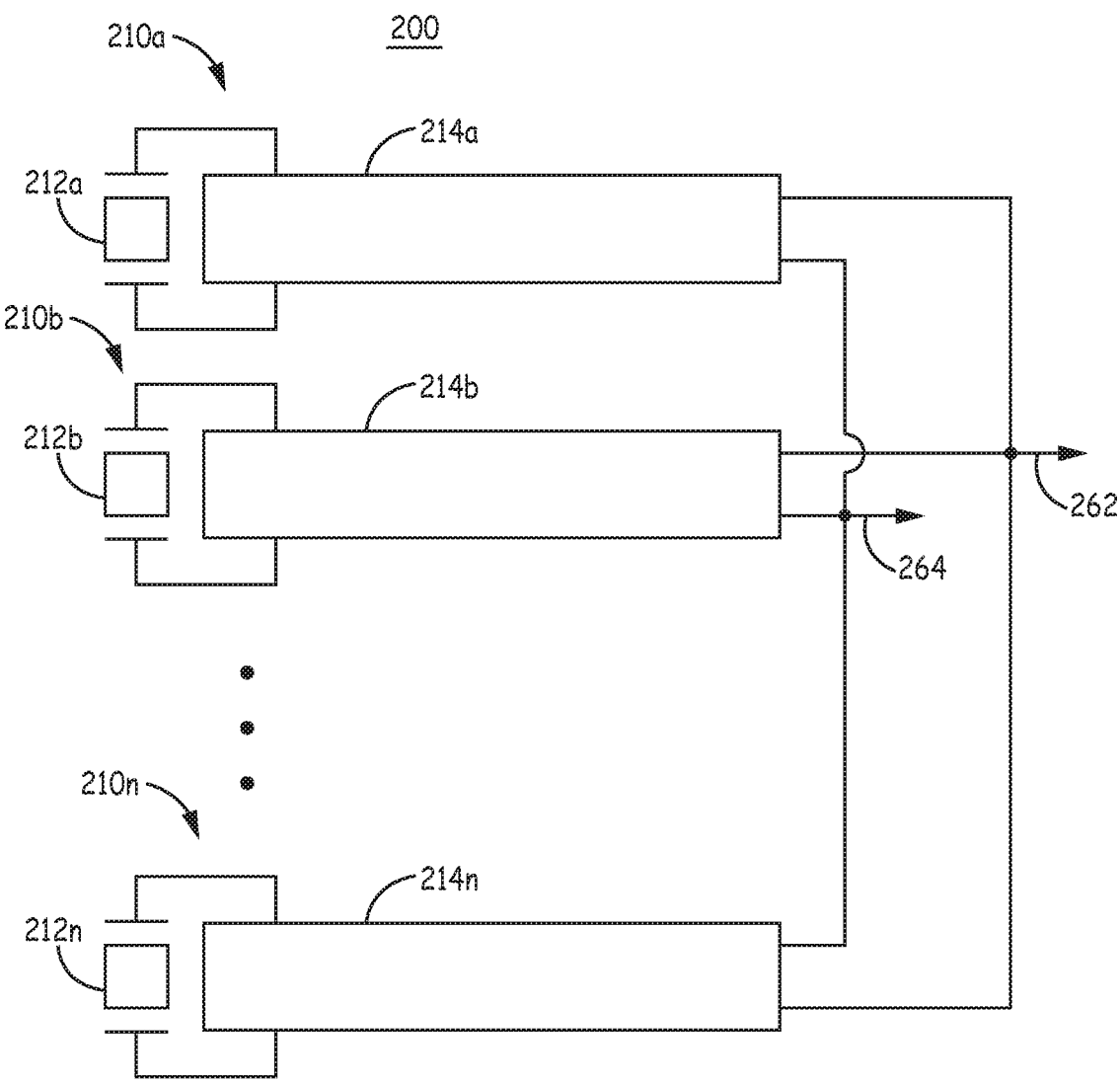
FIG. 7 is a schematic diagram of the circuitry that may be included in the pulse delivery device of FIG. 1 according to another example.

In some examples, the circuitry shown in FIG. 5 or FIG. 6 is provided as a single solid-state, integrated circuit with piezoelectric element 112 comprising an array of piezoelectric elements in series and/or in parallel having outputs coupled to the Zener diodes or other circuitry implemented as a rectifier 104 as shown in FIG. 4. In other examples, as shown by the conceptual diagram of pulse generator 200 in FIG. 7, the circuitry shown in FIG. 5 or FIG. 6 may be a unit 210 that is repeated multiple times within pulse delivery device 200. Each unit, 210a, 210b, through 210n, collectively 210, may have a single piezoelectric element 112, or a combination of piezoelectric elements, coupled to a rate limiting and filtering circuit 214a through 214n. Circuits 214a-n may each correspond to the circuitry shown in FIG. 5 or 6, including each of the components of FIG. 5 or 6 as described above for rectifying, low pass filtering, rate limiting, and high pass filtering the voltage signal produced by each respective piezoelectric element 210a-n. The outputs of each unit 210a-n is coupled in parallel to pacing electrodes 264 and 262 for delivering pacing pulses to a patient's heart. The values of the various components included in each unit 210a-n, e.g., values corresponding to resistors R1 132 and R2 142 and capacitors C1 130, C2 140 and C3 154 may be selected according to the RC time constants required for the individual units 210a-n coupled in parallel. These values will be different from the values of the various components used in the circuit of FIG. 5 or FIG. 6 when provided as the sole circuit in pulse delivery device 100 coupled to piezoelectric element 112. By providing multiple, repeated units 210a-n coupled in parallel to pacing electrodes 262 and 264, the volume and geometry of the housing of pulse delivery device 200 may be minimized and utilized more efficiently.

Thus, an implantable medical device system including an electrical stimulation pulse delivery device have been presented in the foregoing description with reference to specific examples. It is appreciated that various modifications to the referenced examples may be made, including modifying the order or combinations of circuit components and functionality shown in the drawings presented herein, to successfully block diagnostic ultrasound energy from being delivered by a passive pulse delivery device that converts ultrasound energy received from an implantable sensing and power transmitting device to electrical stimulation pulses delivered to a patient's body. Such modifications may be made without departing from the scope of the following claims.

The invention claimed is:

1. An implantable device for delivering electrical stimulation pulses to a patient's body, comprising:
a housing;
a pair of electrodes carried by the housing;
a piezoelectric element that is enclosed by the housing and produces voltage signals in response to receiving ultrasound energy transmitted through the patient's body; and
a circuit coupled to the piezoelectric element and configured to pass at least a portion of the voltage signals produced by the piezoelectric element to the pair of electrodes for delivering an electrical stimulation pulse to the patient's body, the circuit comprising a rate limiter configured to filter a voltage signal produced by the piezoelectric element that occurs at an interval less than a maximum pulse rate interval after a preceding voltage signal has been passed to the pair of electrodes.

2. The device of claim 1, wherein the circuit comprises a shunt configured to shunt a voltage signal produced by the piezoelectric element away from the electrode pair if the voltage signal produced by the piezoelectric element is longer than a maximum electrical stimulation pulse duration.

3. The device of claim 1, wherein the circuit comprises a low pass filter that filters a voltage signal produced by the piezoelectric element having a pulse duration that is less than a minimum electrical stimulation pulse duration.

4. The device of claim 1, wherein the circuit comprises a rectifier configured to receive the voltage signals produced by the piezoelectric element and pass the voltage signals to the rate limiter as rectified voltage signals.

5. The device of claim 1, wherein the circuit comprises a voltage limiter that limits a maximum voltage of the voltage signals passed to the pair of electrodes.

6. The device of claim 1, wherein the circuit comprises a high pass filter coupled to the rate limiter and configured to pass a voltage signal received from the rate limiter having a pulse duration up to a maximum pulse duration to the pair of electrodes.

7. The device of claim 1, further comprising a plurality of piezoelectric elements coupled to the circuit.

8. The device of claim 1, further comprising a plurality of piezoelectric elements and a plurality of circuits, each piezoelectric element coupled to a respective one of the plurality of circuits, each of the plurality of respective circuits comprising a respective rate limiter that is coupled to the pair of electrodes.

9. The device of claim 1, wherein the circuit further comprises:
a first filter configured to filter first voltage signals produced by the piezoelectric element in response to receiving diagnostic ultrasound bursts having a pulse duration less than a minimum electrical stimulation pulse duration;
a second filter configured to filter second voltage signals produced by the piezoelectric element in response to receiving diagnostic ultrasound bursts having a pulse duration greater than a maximum electrical stimulation pulse duration, and
the rate limiter comprising a shunt configured to shunt current in the circuit away from the pair of electrodes in response to third voltage signals produced by the piezoelectric element receiving diagnostic ultrasound signals at a rate that is greater than the maximum pulse rate interval.

10. The device of claim 1, wherein the device is a cardiac pacing pulse delivery device and the maximum pulse rate interval is a maximum cardiac pacing rate interval.

11. The device of claim 1, wherein the rate limiter comprises:
a peak detector configured to detect voltage signal peaks greater than a voltage threshold; and
a shunt configured to shunt pulses detected by the peak detector and occurring at a rate faster than a maximum pulse rate away from the pair of electrodes.

12. An implantable medical device system for delivering electrical stimulation pulses to a patient's body, comprising:
an implantable pulse delivery device; and
a second implantable device comprising an array of ultrasound transducers, a control circuit, and a first housing enclosing the array of ultrasound transducers and the control circuit, the control circuit configured to control the array to transmit ultrasound signals at a pulse delivery rate to the implantable pulse delivery device;
the implantable pulse delivery device comprising:
a second housing;
a pair of electrodes carried by the second housing;
a piezoelectric element that is enclosed by the housing and produces voltage signals in response to receiving ultrasound energy transmitted through the patient's body; and
a circuit coupled to the piezoelectric element and configured to pass at least a portion of the voltage signals produced by the piezoelectric element to the pair of electrodes for delivering an electrical stimulation pulse to the patient's body, the circuit comprising a rate limiter configured to filter a voltage signal produced by the piezoelectric element that occurs at an interval less than a maximum pulse rate interval after a preceding voltage signal has been passed to the pair of electrodes.

13. The system of claim 12, wherein the circuit comprises a shunt configured to shunt a voltage signal produced by the piezoelectric element away from the electrode pair if the voltage signal produced by the piezoelectric element is longer than a maximum electrical stimulation pulse duration.

14. The system of claim 12, wherein the circuit comprises a low pass filter that filters a voltage signal produced by the piezoelectric element having a pulse duration that is less than a minimum electrical stimulation pulse duration.

15. The system of claim 12, wherein the circuit comprises a rectifier configured to receive the voltage signals produced by the piezoelectric element and pass the voltage signals to the rate limiter as rectified voltage signals.

16. The system of claim 12, wherein the circuit comprises a voltage limiter that limits a maximum voltage of the voltage signals passed to the pair of electrodes.

17. The system of claim 12, wherein the circuit comprises a high pass filter coupled to the rate limiter and configured to pass a voltage signal received from the rate limiter having a pulse duration up to a maximum pulse duration to the pair of electrodes.

18. The system of claim 12, further comprising a plurality of piezoelectric elements coupled to the circuit.

19. The system of claim 12, further comprising a plurality of piezoelectric elements and a plurality of circuits, each piezoelectric element coupled to a respective one of the plurality of circuits, each of the plurality of respective circuits comprising a respective rate limiter that is coupled to the pair of electrodes.

20. The system of claim 12, wherein the circuit further comprises:
a first filter configured to filter first voltage signals produced by the piezoelectric element in response to receiving diagnostic ultrasound bursts having a pulse duration less than a minimum electrical stimulation pulse duration; and
a second filter configured to filter second voltage signals produced by the piezoelectric element in response to receiving diagnostic ultrasound bursts having a pulse duration greater than a maximum electrical stimulation pulse duration, and
the rate limiter comprising a shunt configured to shunt current in the circuit away from the pair of electrodes in response to third voltage signals produced by the piezoelectric element receiving diagnostic ultrasound signals at a rate that is greater than the maximum pulse rate interval.

21. The system of claim 12, wherein the first implantable device is a cardiac pacing pulse delivery device and the maximum pulse rate interval is a maximum cardiac pacing rate interval.

22. The system of claim 12, wherein the rate limiter comprises:
a peak detector configured to detect voltage signal peaks greater than a voltage threshold; and
a shunt configured to shunt pulses detected by the peak detector and occurring at a rate faster than a maximum pulse rate away from the pair of electrodes.

23. An implantable medical device system for delivering electrical stimulation pulses to a patient's body, comprising:
a first implantable device; and
a second implantable device comprising an array of ultrasound transducers, a control circuit, and a first housing enclosing the array of ultrasound transducers and the control circuit, the control circuit configured to control the array to transmit ultrasound signals at an electrical stimulation pulse delivery rate to the first device;
the first implantable device comprising:
a second housing;
a pair of electrodes carried by the second housing;
a piezoelectric element enclosed by the housing and configured to produce a voltage signal in response to receiving ultrasound energy transmitted through a patient's body, the piezoelectric element, wherein the ultrasound energy comprises first ultrasound signals transmitted by the second implantable device and second, diagnostic ultrasound signals transmitted through the patient's body; and
a circuit coupled to the piezoelectric element and configured to:
deliver electrical stimulation pulses to the patient's body by passing a first portion of the voltage signals produced by the piezoelectric element in response to the first ultrasound signals transmitted by the second implantable device to the pair of electrodes, and
filter a second portion of the voltage signals from being passed to the pair of electrodes, the second portion of the voltage signals produced by the piezoelectric element in response to the second, diagnostic ultrasound signals.

* * * * *